US009409990B2

(12) United States Patent
Zhang

(10) Patent No.: US 9,409,990 B2
(45) Date of Patent: Aug. 9, 2016

(54) METHODS OF INHIBITING TUMOR GROWTH BY ANTAGONIZING IL-6 RECEPTOR

(71) Applicant: Regeneron Pharmaceuticals, Inc., Tarrytown, NY (US)

(72) Inventor: Li Zhang, Baldwin Place, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/329,565

(22) Filed: Jul. 11, 2014

(65) Prior Publication Data

US 2014/0322215 A1    Oct. 30, 2014

Related U.S. Application Data

(63) Continuation of application No. 13/672,923, filed on Nov. 9, 2012, now abandoned.

(60) Provisional application No. 61/557,939, filed on Nov. 10, 2011, provisional application No. 61/609,968, filed on Mar. 13, 2012, provisional application No. 61/613,538, filed on Mar. 21, 2012.

(51) Int. Cl.
| | |
|---|---|
| C07K 16/28 | (2006.01) |
| A61K 39/395 | (2006.01) |
| C07K 16/22 | (2006.01) |
| C07K 19/00 | (2006.01) |
| C07K 16/32 | (2006.01) |
| A61K 39/00 | (2006.01) |

(52) U.S. Cl.
CPC ......... *C07K 16/2866* (2013.01); *A61K 39/3955* (2013.01); *A61K 39/39558* (2013.01); *C07K 16/22* (2013.01); *C07K 16/2863* (2013.01); *C07K 16/32* (2013.01); *C07K 19/00* (2013.01); *A61K 2039/505* (2013.01); *A61K 2039/507* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,480,796 | A | 1/1996 | Kishimoto |
| 5,670,373 | A | 9/1997 | Kishimoto |
| 5,795,965 | A | 8/1998 | Tsuchiya et al. |
| 5,817,790 | A | 10/1998 | Tsuchiya et al. |
| 5,888,510 | A | 3/1999 | Kishimoto et al. |
| 6,086,874 | A | 7/2000 | Yoshida et al. |
| 6,410,691 | B1 | 6/2002 | Kishimoto |
| 7,396,664 | B2 | 7/2008 | Daly et al. |
| 7,582,298 | B2 | 9/2009 | Stevens et al. |
| 8,043,617 | B2 | 10/2011 | Stevens et al. |
| 8,080,248 | B2 | 12/2011 | Radin et al. |
| 8,183,014 | B2 | 5/2012 | Stevens et al. |
| 8,192,741 | B2 | 6/2012 | Radin et al. |
| 2007/0134242 | A1 | 6/2007 | Nishimoto |
| 2007/0243189 | A1 | 10/2007 | Yoshizaki |
| 2010/0129357 | A1 | 5/2010 | Garcia-Martinez et al. |

FOREIGN PATENT DOCUMENTS

| | | |
|---|---|---|
| EP | 1967209 | 6/2012 |
| WO | 2010065079 | 6/2010 |

OTHER PUBLICATIONS

Hsu et al, Biodrugs; 2009; vol. 23, No. 5, pp. 289-304.*
Agarwala and Case, "Everolimus (RAD001) in the Treatment of Advanced Renal Cell Carcinoma: A Review," The Oncologist, Mar. 2010, 15:236-245.
Barre et al., "The STAT3 oncogene as predictive marker of drug resistance," TRENDS Mol. Med., Nov. 2006, 13 (1):4-11.
Berishaj et al., "Stat3 is tyrosine-phosphorylated through the interleukin-6/glycoprotein 130/Janus kinase pathway in breast cancer," Breast Cancer Research, May 2007, Epub 9:R32, doi: 10.1186/bcr1680.
Coward et al., "Interleukin-6 as a Therapeutic Target in Human Ovariam Cancer," Clin. Cancer Res., Jul. 2011, 17 (18):6083-6096.
Dalwadi et al., "Cyclooxygenase-2-Dependent Activation of Signal Tranducer and Activator of Transcription 3 by Interleukin-6 in Non-Small Cell Lung Cancer" Clinical Cancer Research, 2006, 11:7674-7682.
Grepin and Pages, "Molecular Mechanisms of Resistance to Tumour Anti-Angiogenic Strategies," J. Oncology, Mar. 2010, Epub 835680, doiL 10.1155/2010/835680.
Hirata et al., "Characterization of IL-6 Receptor Expression by Monoclonal and Polyclonal Antibodies," J. Immunol., Nov. 1989, 143:2900-2906.
Hong et al., "Interleukin-6 and Its Receptor in Cancer, Implications for Translational Therapeutics," Cancer, Nov. 2007, 110(9):1911-1928.
Jain et al., "Biomarkers of response and resistance to antiangiogenic therapy" Nature Reviews Clinical Oncology (Jun. 1, 2009) 6(6):327-338.
Knupfer and Preiss, "Significance of interleukin-6 (IL-6) in breast cancer (review)," Breast Cancer Res. Treat., 2007, 102:129-135.
Mankan and Greten, "Inhibiting signal transducer and activator of transcription 3: rationality and rationale design of inhibitors," Expert Opin. Invest. Drugs, Jan. 2011, 20(9):1263-1275.
Saidi et al., "Combined Targeting of Interleukin-6 and VAscular Endothetial Growth Factor Potently Inhibits Glioma Growth and Invasiveness," Int. J. Cancer, Feb. 2009, 125:1054-1064.

(Continued)

*Primary Examiner* — Bridget E Bunner
*Assistant Examiner* — Fozia Hamud
(74) *Attorney, Agent, or Firm* — Frank Cottingham; Anna D. DiGabriele-Petti; Karl Bozicevic

(57) ABSTRACT

The present invention provides methods for inhibiting or attenuating tumor growth in a subject by administering an IL-6 antagonist to the subject. In certain embodiments, the methods of the invention are used to inhibit the growth of an anti-VEGF-resistant tumor in a subject. The IL-6 antagonist may be, e.g., an antibody that specifically binds IL-6R. The IL-6 antagonist may be administered in combination with a VEGF antagonist, and/or an EGFR antagonist.

24 Claims, 2 Drawing Sheets

(56) References Cited

OTHER PUBLICATIONS

Shinriki et al., "Humanized Anti-Interleukin-6 Receptor Antibody Suppresses Tumor Angiogensis and In Vivo Growth of Human Oral Squamous Cell Carcinoma" Clinical Cancer Research, The American Associate for Cancer Research, US (Sep. 1, 2009) 15(17):5426-5434.

Tabernero, Joseph, "The Role of VEGF and EGFR Inhibition: Implications for Combining Anti-VEGF and Anti-EGFR Agents" Molecular Cancer Research, 2007, 5(3):203-220.

Taga et al., "Interleukin-6 Triggers the Association of Its Receptor with a Possible Signal Transducer, gp130," Cell, Aug. 1989, 58:573-581.

Tohnya and Figg, "Immunomodulation of Multiple Myeloma," Cancer Biology & Therapy, Nov. 2004, 3 (11)1060-1061.

Trikha et al., "Targeted Anti-Interleukin-6 Monoclonal Antibody Therapy for Cancer: A Review of the Rationale and Clinical Evidence," Clin. Cancer Res., Oct. 2003, 9:4653-4665.

Weidle et al., "Interleukin 6/Interleukin 6 Receptor Interaction and its Role as a Therapeutic Target for Treatment of Cachexia and Cancer," Cancer Genomics & Proteomics, 2010, 7:287-302.

Yao et al., "TGF-beta IL-6 Axis Mediates Selective and Adaptive Mechanisms of Resistance to Molecular Targeted Therapy in Lung Cancer," Aug. 2010, 107(35):15535-15540.

* cited by examiner

US 9,409,990 B2

METHODS OF INHIBITING TUMOR GROWTH BY ANTAGONIZING IL-6 RECEPTOR

CROSS-REFERENCE TO RELATED APPLICATIONS

This application is a continuation of U.S. patent application Ser. No. 13/672,923 filed Nov. 9, 2012, now abandoned, which application claims the benefit of priority under 35 U.S.C. §119(e) of US provisional application Nos. 61/557,939 filed on Nov. 10, 2011; 61/609,968, filed on Mar. 13, 2012; and 61/613,538 filed on Mar. 21, 2012, the disclosures of which are herein incorporated by reference in their entireties.

FIELD OF THE INVENTION

The present invention relates to compositions and methods for inhibiting or attenuating tumor growth or proliferation in a subject. More specifically, the invention relates to methods comprising administering an interleukin-6 (IL-6) antagonist to a tumor-bearing subject.

BACKGROUND

Antagonists of vascular endothelial growth factor (VEGF) have been shown to effectively inhibit tumor growth in numerous experimental and clinical settings. VEGF antagonists exert their therapeutic effects by targeting the tumor vasculature. It has been observed, however, that tumors under certain circumstances can develop resistance to anti-VEGF agents. Thus, there is a need in the art for new therapeutic approaches for treating tumors, including methods of inhibiting the growth of tumors that have developed resistance to anti-VEGF therapies.

Interleukin-6 ("IL-6") is a pro-inflammatory cytokine that is expressed in multiple cancer types. Clinical studies have shown that increased serum IL-6 levels are associated with worse patient outcomes. Elevated expression of IL-6 can result from the activation of oncogenic signaling pathways and/or as a consequence of chronic inflammation, which has been associated with the development of cancer. IL-6 signals through its heterodimeric receptor IL-6R/gp130 to activate the JAK/STAT and Ras signaling pathways. In particular, IL-6 strongly activates STAT3, which has been shown to promote tumor cell proliferation, invasion and survival. Inhibition of IL-6 signaling with monoclonal antibodies directed against IL-6 or IL-6R has been shown to inhibit tumor growth in several preclinical models, suggesting that the IL-6 pathway is an attractive therapeutic target for cancer. An association between IL-6 levels and anti-VEGF resistance, or the use of IL-6 antagonists to treat anti-VEGF resistant tumors, however, has not been described.

BRIEF SUMMARY OF THE INVENTION

The present invention is based, at least in part, on the surprising discovery that anti-VEGF-resistant tumors express elevated levels of IL-6 and that antagonism of IL-6 (e.g., by using an anti-IL-6R antibody), when combined with anti-VEGF therapy, is able to overcome anti-VEGF resistance in tumors and thus provides robust anti-tumor activity against tumors that heretofore were deemed unresponsive to VEGF antagonism.

Thus, according to one aspect of the present invention, methods and compositions are provided for inhibiting or attenuating the growth of an anti-VEGF-resistant tumor in a subject. According to certain embodiments of this aspect of the invention, methods of cancer therapy are provided comprising: (i) measuring the level of IL-6/STAT3 signaling in a tumor biopsy from a subject; and (ii) administering an IL-6 antagonist to the subject if the tumor biopsy exhibits increased IL-6/STAT3 signaling. The methods according to this aspect of the invention also comprise administering to the subject an IL-6 antagonist and a VEGF antagonist. In accordance with this aspect of the invention, compositions are provided which comprise at least one IL-6 antagonist and at least one VEGF antagonist.

According to another aspect of the present invention, methods are provided for enhancing the anti-tumor activity of an IL-6 antagonist. The methods according to this aspect of the invention comprise administering at least one additional anti-tumor agent to a tumor-bearing subject in combination with an IL-6 antagonist. The additional anti-tumor agent can be, e.g., a VEGF antagonist, an EGFR antagonist, or a combination thereof.

The antagonist molecules of the invention can be, e.g., antigen-specific binding proteins, including antigen-specific binding proteins that specifically bind, e.g., IL-6, IL-6R, VEGF, VEGFR1, VEGFR2, EGFR, EGFRvIII, ErbB2, ErbB3, and/or ErbB4. Antigen-specific binding proteins of the present invention include antibodies and antigen-binding fragments thereof. Antigen-specific binding proteins also include fusion polypeptides comprising ligand-binding portions of one or more receptor molecules. In certain exemplary embodiments, the IL-6 antagonist is an antibody that specifically binds IL-6R, the VEGF antagonist is a VEGF-binding fusion molecule comprising VEGF binding domains of VEGFR1, VEGFR2 and a multimerizing domain (a "VEGF-Trap"), and the EGFR antagonist is an antibody that specifically binds EGFR (ErbB1/HER1), or an antibody that specifically binds ErbB3, or an antibody that specifically binds ErbB4. However, other antagonists can be used in the context of the present invention as described elsewhere herein.

Other embodiments of the present invention will become apparent from a review of the ensuing detailed description.

BRIEF DESCRIPTION OF THE FIGURES

FIG. 2, panel B shows the results of a Western blot performed on A431-P or A431-V2 cells treated with either hFc control protein (10 μg/ml) or anti-IL-6R mAb1 (10 μg/ml), to measure the levels of phospho-STAT3 (relative to actin control).

DETAILED DESCRIPTION

Figure 1:
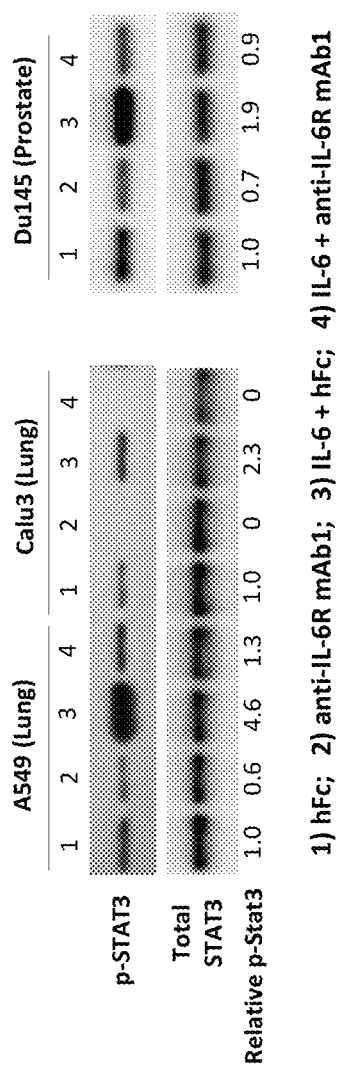
FIG. 1 shows the results of Western blots on cultured A549, Calu3 and Du145 tumor cells to assess the levels of phospho-STAT3 and total STAT3 in the cells following treatment with 10 μg/ml human Fc control protein (lane 1), 10 μg/ml anti-IL-6R mAb1 (lane 2), 10 ng/ml IL-6 plus 10 μg/ml hFc (lane 3), or 10 ng/ml IL-6 plus 10 μg/ml anti-IL-6R mAb1 (lane 4).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Methods for Inhibiting or Attenuating Tumor Growth

The present invention provides methods for inhibiting or attenuating the growth of a tumor in a subject. The invention includes administering an IL-6 antagonist to a tumor-bearing subject. The IL-6 antagonist may be administered in combination with one or more additional therapeutic agents. Exemplary therapeutic agents that can be administered in combination with an IL-6 antagonist, in accordance with the methods of the present invention, include, e.g., antagonists of vascular endothelial growth factor (VEGF) and/or epidermal growth factor receptor (EGFR) antagonists (as defined herein). Further examples of therapeutic agents that can be administered in combination with an IL-6 antagonist in accordance with the methods of the present invention are described elsewhere herein.

The methods of the present invention are useful for the treatment of primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. Specific cancers that are treatable according to the methods of the present invention include, e.g., renal cell carcinoma, pancreatic carcinoma, breast cancer, prostate cancer, hepatocellular carcinoma, colorectal cancer, malignant mesothelioma, multiple myeloma, ovarian cancer, and melanoma.

In certain embodiments, the methods of the present invention are useful for the treatment of anti-VEGF-resistant tumors in a subject. An "anti-VEGF-resistant tumor," as used herein, means a tumor that does not respond, or only partially responds, to treatment with an anti-VEGF agent such as an anti-VEGF antibody, an anti-VEGF receptor antibody, or any other VEGF-specific binding protein (including, e.g., a VEGF-trap, as defined herein). For example, an anti-VEGF-resistant tumor can be, e.g., a tumor that, when contacted with an amount of VEGF antagonist that is ordinarily capable of inhibiting or attenuating the growth of at least one type of tumor, continues to grow and/or proliferate in vitro or in vivo (e.g., in cell culture or when implanted into an animal). An anti-VEGF-resistant tumor may be a tumor derived from tumor cells that originally responded to anti-VEGF therapy, but through selection, mutation or adaptation, have acquired resistance to one or more anti-VEGF agents.

The subjects that are treatable using the methods of the present invention include any subject diagnosed with cancer or identified as having a tumor. In certain embodiments, the subject is a patient who has been diagnosed or identified as having a tumor that is at least partially resistant to anti-VEGF treatment. Methods for diagnosing a patient as having an anti-VEGF resistant tumor will be known to persons of ordinary skill in the art and can be practiced using routine diagnostic methods.

As shown in the Examples herein, tumor cells that are resistant to anti-VEGF therapy are shown to express higher levels of IL-6 and phospho-STAT3 than the parental non-resistant tumor cells. Thus, the present invention also includes methods of cancer therapy comprising: (i) measuring the level of IL-6/STAT3 signaling in a subject (e.g., in a serum sample, tissue sample, tumor biopsy, etc., obtained from the subject); and (ii) administering an IL-6 antagonist to the subject if the subject (or sample/biopsy obtained therefrom) exhibits increased IL-6/STAT3 signaling.

According to certain embodiments of the present invention, the expression "increased IL-6/STAT-3 signaling" means that the amount of IL-6 and/or amount of phospho-STAT3 measured in a tumor biopsy is at least 3× higher (e.g., 4×, 5×, 6×, 7× or more) than in a tumor that is sensitive (i.e., not resistant) to anti-VEGF therapy. According to certain embodiments of the present invention, "increased IL-6/STAT-3 signaling" means that the ratio of phospho-STAT3 to an invariant control protein (e.g., the P-STAT3/actin ratio) in a sample taken from a subject is greater than about 2.0, 2.5, 3.0, 3.5, 4.0, 4.5, 5.0, 5.5, 6.0, 6.5, 7.0, 7.5, or more. According to certain embodiments of the present invention, "increased IL-6/STAT-3 signaling" means that the concentration of IL-6 in a tumor sample taken from a subject is greater than about 50 µg/ml, 55 µg/ml, 60 µg/ml, 65 µg/ml, 70 pg/ml, 75 pg/ml, 80 pg/ml, 85 pg/ml, 90 pg/ml, 95 pg/ml, 100 pg/ml, 110 pg/ml, 120 pg/ml, 130 pg/ml, 140 pg/ml, 150 pg/ml, 160 pg/ml, 170 pg/ml, 180 pg/ml, 190 pg/ml, 200 pg/ml, or higher. Levels of IL-6 and phospho-STAT3 can be measured, e.g., using Western blot, ELISA, or by any other immunohistochemical methodology known in the art.

Similarly, the present invention also includes methods for determining whether a tumor-bearing patient has an anti-VEGF-resistant tumor. Methods according to this aspect of the invention comprise measuring the level of IL-6/STAT3 signaling in a sample (e.g., tumor biopsy) from a patient, wherein "increased IL-6/STAT3 signaling" in the sample (as that expression is defined herein above) identifies the subject as having an anti-VEGF-resistant tumor. Since the present inventors have demonstrated that anti-VEGF-resistant tumors are sensitive to IL-6 antagonism, the methods according to this aspect of the invention may, in certain embodiments, further comprise administering to the patient an IL-6 antagonist and/or a VEGF antagonist.

Antagonists

The present invention includes methods that comprise administering an IL-6 antagonist, a VEGF antagonist, an EGFR antagonist, and/or combinations thereof, to a subject in need thereof. As used herein, an "IL-6 antagonist" is any agent which binds to or interacts with IL-6 and inhibits the normal biological signaling function of IL-6 in vitro or in vivo. The term "IL-6 antagonist" also includes antagonists of IL-6 receptor ("IL-6R", i.e., "IL-6R antagonists). An IL-6R antagonist may be any agent which binds to or interacts with IL-6R and inhibits the normal biological signaling function of IL-6R in vitro or in vivo.

A VEGF antagonist can be any agent which binds to or interacts with VEGF or a VEGF receptor (VEGFR1, also referred to as Flt1; or VEGFR2, also referred to as Flk1 or KDR).

An EGFR antagonist can be any agent which binds to or interacts with an epidermal growth factor receptor and inhibits the normal biological signaling function of the receptor in vitro or in vivo. The expression "EGFR antagonist," as used herein, includes antagonists of any one or more members of the epidermal growth factor receptor family. For example, an EGFR antagonist may be an antagonist of EGFR (also referred to as ErbB1 or HER1), an antagonist of a variant of EGFR such as, e.g., EGFRvIII, an antagonist of ErbB2 (also referred to as HER2 or Neu), an antagonist of ErbB3 (also referred to as HER3), and/or an antagonist of ErbB4 (also referred to as HER4).

Antagonists of IL-6, IL-6R, VEGF, VEGF receptors, and EGFRs include small molecule antagonists, as well as antigen-specific binding proteins, as described elsewhere herein.

Antigen-Specific Binding Proteins

The antagonists that are useful in the methods of the present invention include antigen-specific binding proteins. For example, the present invention includes methods comprising administering an antigen-specific binding protein that specifically binds interleukin-6 (IL-6) or IL-6 receptor (IL-6R) to a subject. The present invention also includes methods comprising administering an antigen-specific binding protein that specifically binds vascular endothelial growth factor (VEGF), or a VEGF receptor (VEGFR), or an antigen-specific binding protein that specifically binds epidermal growth factor receptor (EGFR, EGFRvIII, ErbB2, ErbB3, and/or ErbB4) to a subject.

As used herein, the expression "antigen-specific binding protein" means a protein comprising at least one domain which specifically binds a particular antigen. Exemplary categories of antigen-specific binding proteins include antibodies, antigen-binding portions of antibodies, peptides that specifically interact with a particular antigen (e.g., peptibodies), receptor molecules that specifically interact with a particular antigen, and proteins comprising a ligand-binding portion of a receptor that specifically binds a particular antigen.

The term "specifically binds" or the like, as used herein, means that an antigen-specific binding protein, or an antigen-specific binding domain, forms a complex with a particular antigen characterized by a dissociation constant ($K_D$) of 500 pM or less, and/or does not bind other unrelated antigens under ordinary test conditions. "Unrelated antigens" are proteins, peptides or polypeptides that have less than 75% amino acid identity to one another. Methods for determining whether two molecules specifically bind one another are well known in the art and include, for example, equilibrium dialysis, surface plasmon resonance, and the like. For example, an antigen-specific binding protein or an antigen-specific binding domain, as used in the context of the present invention, includes molecules that bind a particular antigen (e.g., IL-6, IL-6R, VEGF, VEGFR and/or EGFR) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

As used herein, an antigen-specific binding protein or antigen-specific binding domain "does not bind" to an unrelated antigen if the protein or binding domain, when tested for binding to the unrelated antigen at 25° C. in a surface plasmon resonance assay, exhibits a $K_D$ of greater than 1000 pM, or fails to exhibit any binding in such an assay or equivalent thereof.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies and Antigen-Binding Fragments of Antibodies

As indicated above, an antigen-specific binding protein can comprise or consist of an antibody or antigen-binding fragment of an antibody that specifically binds a particular antigen (e.g., anti-IL-6 antibody, anti-IL-6R antibody, anti-VEGF antibody, anti-VEGFR antibody and/or anti-EGFR antibody, or antigen-binding fragments thereof).

The term "antibody", as used herein, includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_{H1}$-$C_H2$; (v) $V_H$-$C_{H1}$-$C_{H2}$-$C_H3$; (vi) $V_H$-$C_{H2}$-$C_H3$; (vii) $V_H$-$C_L$; (viii) $V_L$-$C_H1$; (ix) $V_L$-$C_H2$; (x) $V_L$-$C_H3$; (xi) $V_L$-$C_{H1}$-$C_H2$; (xii) $V_L$-$C_H1$-$C_H2$-$C_H3$, (xiii) $V_L$-$C_{H2}$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Anti-IL-6R Antibodies and Antigen-Binding Fragments Thereof

The methods of the present invention, according to certain embodiments, comprises administering an anti-IL-6R antibody, or antigen-binding fragment thereof, to a subject. The terms "interleukin-6 receptor", "IL-6R", and the like, as used herein, are intended to refer to a human cytokine receptor that specifically binds interleukin-6 (IL-6). The extracellular domain of human IL-6R has the amino acid sequence as set forth in SEQ ID NO:1. Anti-IL-6R antibodies are mentioned in, e.g., U.S. Pat. Nos. 5,795,695; 5,817,790; 6,410,691; 6,670,373; and 7,582,298. Any of the anti-IL-6R antibodies mentioned and/or described in any of the foregoing publications, or antigen-binding fragments thereof, can be used in the context of the present invention. A non-limiting, exemplary anti-IL-6R antibody that can be used in the context of the present invention is an anti-IL-6R antibody, or antigen-binding fragment thereof, comprising the heavy and light chain CDRs of the HCVR/LCVR amino acid pair comprising SEQ ID NOs: 2/3. For example, the anti-IL-6R antibody can be an antibody, or antigen-binding fragment thereof, comprising heavy chain CDRs (HCDR1, HCDR2 and HCDR3) having the amino acid sequences of SEQ ID NOs: 4, 5, and 6, respectively; and light chain CDRs (LCDR1, LCDR2 and LCDR3) having the amino acid sequences of SEQ ID NOs: 7, 8, and 9, respectively.

VEGF Antagonists

The methods of the present invention, according to certain embodiments, comprises administering a VEGF antagonist to a subject. As used herein, the expression "VEGF antagonist" means any molecule that blocks, reduces or interferes with the normal biological activity of VEGF. VEGF antagonists include molecules which interfere with the interaction between VEGF and a natural VEGF receptor, e.g., molecules which bind to VEGF or a VEGF receptor and prevent or otherwise hinder the interaction between VEGF and a VEGF receptor. Specific exemplary VEGF antagonists include anti-VEGF antibodies, anti-VEGF receptor antibodies, and VEGF receptor-based chimeric molecules (also referred to herein as "VEGF-Traps").

VEGF receptor-based chimeric molecules include chimeric polypeptides which comprise two or more immunoglobulin (Ig)-like domains of a VEGF receptor such as VEGFR1 (also referred to as Flt1) and/or VEGFR2 (also referred to as Flk1 or KDR), and may also contain a multimerizing domain (e.g., an Fc domain which facilitates the multimerization [e.g., dimerization] of two or more chimeric polypeptides). An exemplary VEGF receptor-based chimeric molecule is a molecule referred to as VEGFR1R2-FcΔC1(a) which is encoded by the nucleic acid sequence of SEQ ID NO:10. VEGFR1R2-FcΔC1(a) comprises three components: (1) a VEGFR1 component comprising amino acids 27 to 129 of SEQ ID NO:11; (2) a VEGFR2 component comprising amino acids 130 to 231 of SEQ ID NO:11; and (3) a multimerization component ("FcΔC1(a)") comprising amino acids 232 to 457 of SEQ ID NO:11 (the C-terminal amino acid of SEQ ID NO:11 [i.e., K458] may or may not be included in the VEGF antagonist used in the methods of the invention; see e.g., U.S. Pat. No. 7,396,664). Amino acids 1-26 of SEQ ID NO:11 are the signal sequence.

Combination Therapies

The methods of the present invention, according to certain embodiments, comprise administering to the subject an IL-6 antagonist in combination with one or more additional therapeutic agent(s) such as a VEGF antagonist and/or an EGFR antagonist. As used herein, the expression "in combination with" means that the additional therapeutic agents are administered before, after, or concurrent with the IL-6 antagonist. For example, when administered "before" the IL-6 antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the IL-6 antagonist. When administered "after" the IL-6 antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the IL-6 antagonist. Administration "concurrent" with the IL-6 antagonist means that the additional therapeutic agent is administered to the subject in a separate dosage form within less than 5 minutes (before, after, or at the same time) of administration of the IL-6 antagonist, or administered to the subject as a single combined dosage formulation comprising both the additional therapeutic agent and the IL-6 antagonist (e.g., a single formulation comprising an anti-IL-6R antibody+a VEGF Trap; or a single formulation comprising an anti-IL-6R antibody+an anti-EGFR antibody; or a single formulation comprising an anti-IL-6R antibody+an anti-ErbB3 antibody; etc.).

Pharmaceutical Compositions and Methods of Administration

The present invention includes pharmaceutical compositions comprising an IL-6 antagonist. The present invention also includes pharmaceutical compositions comprising an IL-6 antagonist and a second active component such as a VEGF antagonist and/or an EGFR antagonist. For example, the present invention includes pharmaceutical compositions comprising an anti-IL-6R antibody and a VEGF-Trap molecule; the present invention also includes pharmaceutical compositions comprising an anti-IL-6R antibody and an anti-EGFR antibody. Methods of treatment comprising administering such pharmaceutical compositions to a patient are also encompassed within the scope of the present invention.

The pharmaceutical compositions of the invention are formulated with suitable carriers, excipients, and other agents that provide suitable transfer, delivery, tolerance, and the like. A multitude of appropriate formulations can be found in, e.g., Remington's Pharmaceutical Sciences, Mack Publishing Company, Easton, Pa. Suitable formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Additional suitable formulations are also described in Powell et al. "Compendium of excipients for parenteral formulations" PDA (1998) J Pharm Sci Technol 52:238-311.

Various delivery systems are known and can be used to administer the pharmaceutical compositions of the present invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical compositions of the present invention can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of active ingredient(s) (e.g., IL-6 antagonist, VEGF antagonist, EGFR antagonist, etc.) that can be administered to a subject is, generally, a therapeutically effective amount. As used herein, the phrase "therapeutically effective amount" means a dose of antigen-specific binding proteins and/or antigen-binding molecules that results in a decrease in tumor growth or weight of at least 5%, relative to a negative control, when administered to a tumor bearing animal (See, e.g., Example 1 herein). For example, a "therapeutically effective amount" of an IL-6R-specific binding protein, a VEGF-specific binding protein, and/or an EGFR-specific binding protein includes, e.g., an amount of such antigen-specific binding protein(s) that, when administered to a tumor bearing animal, causes a decrease in tumor growth or weight of at least 5%, 10%, 15%, 20%, 25%, 30%, 35%, 40%, 45%, 50%, 55%, 60%, 65%, 70%, 80%, 90%, 95%, or 100%, relative to negative control-treated animals.

In the case of antigen-specific binding proteins of the present invention (e.g., anti-IL-6R antibodies, anti-EGFR antibodies, anti-ErbB3 antibodies, and/or VEGF-Trap molecules), a therapeutically effective amount can be from about 0.05 mg to about 600 mg; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the respective antigen-specific binding protein. For example, according to certain specific embodiments in which an anti-IL-6R antibody is administered (e.g., mAb1 discussed herein), the antibody may be administered to a subject at a dose of 100 mg, 150 mg, or 200 mg, (e.g., at a frequency of once a week, once every two weeks, etc.).

The amount of antigen-specific binding proteins of the present invention contained within the individual doses may be expressed in terms of milligrams of antibody per kilogram of patient body weight (i.e., mg/kg). For example, the anti-IL-6R antibodies, anti-EGFR antibodies, anti-ErbB3 antibodies, and/or VEGF-Trap molecules of the present invention may be administered to a patient at a dose of about 0.0001 to about 50 mg/kg of patient body weight (e.g. 0.5 mg/kg, 1.0 mg/kg, 1.5 mg/kg, 5.0 mg/kg, 10 mg/kg, 12.5 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 35 mg/kg, 40 mg/kg, etc.). According to certain exemplary embodiments, the amount of VEGF-Trap molecule administered to the patient in a particular dose is 4 mg/kg or 6 mg/kg.

The active ingredients (e.g., anti-IL-6R antibodies, anti-EGFR antibodies, anti-ErbB3 antibodies, and/or VEGF-Trap molecules) may be present in the compositions of the present invention in equal amounts, or alternatively, may be present in amounts that vary from one another by a factor of 0.5, 1, 1.5, 2, 2.5, 3, 4, 5, or more. A person of ordinary skill in the art, using routine experimentation, will be able to determine the appropriate amounts of the individual components in the compositions of the present invention necessary to produce a desired therapeutic effect.

Administration Regimens

According to certain embodiments of the present invention, multiple doses of the compositions of the present invention (e.g., compositions comprising an IL-6 antagonist, a VEGF antagonist and/or an EGFR antagonist), may be administered to a subject over a defined time course. The methods according to this aspect of the invention comprise sequentially administering to a subject multiple doses of the composition(s) of the present invention. As used herein, "sequentially administering" means that each dose of the composition(s) of the present invention are administered to the subject at a different point in time, e.g., on different days separated by a predetermined interval (e.g., hours, days, weeks or months). The present invention includes methods which comprise sequentially administering to the patient an initial dose of a composition of the present invention, followed by one or more secondary doses of the composition, and optionally followed by one or more tertiary doses of the composition.

The terms "initial dose," "secondary doses," and "tertiary doses," refer to the temporal sequence of administration of the compositions of the present invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of active ingredient(s), but will generally differ from one another in terms of frequency of administration. In certain embodiments, however, the amount of active ingredient(s) contained in the initial, secondary and/or tertiary doses will vary from one another (e.g., adjusted up or down as appropriate) during the course of treatment.

In one exemplary embodiment of the present invention, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose. The phrase "the immediately preceding dose," as used herein, means, in a sequence of multiple administrations, the dose(s) of the compositions of the present invention which are administered to a subject prior to the administration of the very next dose in the sequence with no intervening doses.

The methods according to this aspect of the invention may comprise administering to a patient any number of secondary and/or tertiary doses of the compositions of the present invention. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 29 days after the immediately preceding dose. Similarly, in embodiments involving multiple tertiary doses, each tertiary dose may be administered at the same frequency as the other tertiary doses. For example, each tertiary dose may be administered to the patient 1 to 60 days after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

An Anti-IL-6R Monoclonal Antibody Inhibits Tumor Xenograft Growth as a Single Agent and in Combination with Other Anti-Tumor Agents Therapeutic Agents This example demonstrates the administration of an anti-IL-6R antibody, alone and in combination with a VEGF-Trap, an anti-EGFR antibody or an anti-ErbB3 antibody, to tumor bearing mice. The anti-IL-6R antibody used in this Example, also referred to herein as "anti-IL-6R mAb1," is an antibody comprising heavy chain CDRs (HCDR1, HCDR2 and HCDR3) having the amino acid sequences of SEQ ID NOs: 4, 5, and 6, respectively; and light chain CDRs (LCDR1, LCDR2 and LCDR3) having the amino acid sequences of SEQ ID NOs: 7, 8, and 9, respectively (i.e., the anti-IL-6R antibody designated VQ8F11-21 in U.S. Pat. No. 7,582,298). The VEGF-Trap used in this Example is a dimer of two fusion polypeptides, each comprising: (1) a VEGFR1 component comprising amino acids 27 to 129 of SEQ ID NO:11; (2) a VEGFR2 component comprising amino acids 130 to 231 of SEQ ID NO:11; and (3) a multimerization component ("FcΔC1(a)") comprising amino acids 232 to 457 of SEQ ID NO:11 (i.e., the VEGF-Trap designated VEGFR1R2-FcΔC1(a) in U.S. Pat. No. 7,396,664.) The anti-EGFR antibody used in this Example, also referred to herein as "anti-EGFR mAb2," is a fully human antibody generated against the extracellular domain of human EGFR/ErbB1/HER1. The anti-ErbB3 antibody used in this Example, also referred to herein as "anti-ErbB3 mAb3," is a fully human antibody generated against ErbB3 (i.e., the antibody designated H4H1821N in U.S. patent application Ser. No. 13/623,885, filed on Sep. 21, 2012).

Experimental Procedures and Results

As an initial experiment, cultured A549, Calu3 and Du145 cells were treated with: (i) 10 µg/ml human Fc control protein ("hFc"), (ii) 10 µg/ml of anti-IL-6R mAb1, (iii) 10 ng/ml IL-6 plus 10 µg/ml hFc, or (iv) 10 ng/ml of IL-6 plus 10 µg/ml anti-IL-6R mAb1. Human Fc or anti-IL-6R mAb1 was added into cultured cells for 16 hours, and IL-6 was added into hFc or anti-IL-6R mAb1 pre-treated cells for 30 minutes. Cells were then lysed and Western blots were performed to assess the levels of phospho-STAT3 and total STAT3. As shown in FIG. 1, all three tumor cell lines exhibited both constitutive and IL-6-inducible phospho-STAT3, which was inhibited by anti-IL-6R mAb1.

Next, the effect of anti-IL-6R mAb1, VEGF-Trap, or a combination of anti-IL-6R mAb1 plus VEGF-Trap on the growth of Du145 human prostate carcinoma cells was tested. Briefly, $5 \times 10^6$ Du145 cells (ATCC) were implanted subcutaneously into the flank of 6-8 week old SCID mice (Taconic, Hudson, N.Y.). After tumors reached an average volume of ~200 mm$^3$, mice were randomized into groups for treatment (n=5 mice per group). Mice were administered human Fc control protein (25 mg/kg), anti-IL-6R mAb1 (25 mg/kg), VEGF-Trap (25 mg/kg) or the combination of anti-IL-6R mAb1 plus VEGF-Trap (25+25 mg/kg). All proteins were administered via subcutaneous injection twice per week. Tumor volumes were measured twice per week over the course of the experiment (on days 35, 39, 42, 46, 49, 53, 56, 60, 63 and 67 after implantation). The average tumor growth from the start of treatment was calculated for each group. The percent decrease of tumor growth was calculated from comparison to the Fc control group. The results are summarized in Table 1.

TABLE 1

Inhibition of Du145 tumor xenograft growth in SCID mice

| Antibody (mg/kg) | Tumor growth in mm$^3$ from start of treatment (mean ± SD) | Average % Decrease in Tumor Growth |
|---|---|---|
| hFc control (25) | 517.8 ± 118.8 | — |
| anti-IL-6R mAb1 (25) | 187.1 ± 122.4 | 64 |
| VEGF-trap (25) | −38.1 ± 46.3 | 107 |
| anti-IL-6R mAb1 + VEGF-trap (25 + 25) | −105.7 ± 52.3 | 120 |

An analysis of the raw data underlying the results summarized in Table 1 confirmed that the tumor growth reduction observed in mice treated with the combination of anti-IL-6R mAb1+VEGF-trap was statistically significant in comparison to the reduction observed in mice treated with anti-IL-6R mAb1 alone (p=0.0004).

Du145 tumors from mice treated with hFc (25 mg/kg) or anti-IL-6R mAb1 (25 mg/kg) were excised and sectioned. Immunohistochemistry was performed with antibodies specific to phospho-STAT3 or cleaved caspase 3 as a marker of apoptosis. Tumors treated with anti-IL-6R mAb1 exhibited less staining for phospho-STAT3 and increased staining for cleaved caspase 3, indicating that Du145 tumors have active IL-6/STAT3 signaling that contributes to tumor cell survival. This suggests that IL-6 provides a survival signal to tumor cells.

In a next experiment, the effect of anti-IL-6R mAb1, an inhibitory anti-EGFR antibody ("anti-EGFR mAb2"), or a combination of anti-IL-6R mAb1 plus anti-EGFR mAb2 on the growth of Calu3 human lung adenocarcinoma xenografts was tested. Briefly, $5 \times 10^6$ Calu3 cells (ATCC) were implanted subcutaneously into the flank of 6-8 week old SCID mice (Taconic, Hudson, N.Y.). After tumors reached an average volume of 150-200 mm$^3$, mice were randomized into groups for treatment (n=5 mice per group). Mice were administered human Fc control protein (25 mg/kg), anti-IL-6R mAb1 (12.5 mg/kg), anti-EGFR mAb2 (12.5 mg/kg) or the combination of anti-IL-6R mAb1 plus anti-EGFR mAb2 (12.5+12.5 mg/kg). All proteins were administered via subcutaneous injection twice per week. Tumor volumes were measured twice per week over the course of the experiment (on days 34, 37, 41, 44, 48, 51, 54 and 57 after implantation) and tumor weights were determined upon excision of tumors at the conclusion of the experiment. Averages of the tumor growth from the start of treatment and the tumor weights were calculated for each group. The percent decreases of tumor growth and tumor weight were calculated from comparison to the Fc control group. The results are summarized in Tables 2 and 3.

TABLE 2

Inhibition of Calu3 tumor xenograft growth in SCID mice

| Antibody (mg/kg) | Tumor growth in mm$^3$ from start of treatment (mean ± SD) | Average % Decrease in Tumor Growth |
|---|---|---|
| hFc control (25) | 656.3 ± 202.2 | — |
| anti-IL-6R mAb1 (12.5) | 428.2 ± 122.6 | 35 |
| anti-EGFR mAb2 (12.5) | 335.0 ± 57.6 | 49 |
| anti-IL-6R mAb1 + anti-EGFR mAb2 (12.5 + 12.5) | 147.5 ± 38.6 | 78 |

TABLE 3

Change in Calu3 tumor xenograft weight in SCID mice

| Antibody (mg/kg) | Average Tumor Weight (g) | Average % Decrease in Tumor Weight |
|---|---|---|
| hFc control (25) | 0.884 ± 0.275 | — |
| anti-IL-6R mAb1 (12.5) | 0.836 ± 0.110 | 5 |
| anti-EGFR mAb2 (12.5) | 0.582 ± 0.097 | 34 |
| anti-IL-6R mAb1 + anti-EGFR mAb2 (12.5 + 12.5) | 0.454 ± 0.084 | 49 |

An analysis of the raw data underlying the results summarized in Table 2 confirmed that the tumor growth reduction observed in mice treated with the combination of anti-IL-6R mAb1+anti-EGFR mAb2 was statistically significant in comparison to the reduction observed in mice treated with either anti-IL-6R mAb1 alone (p<0.0001) or anti-EGFR mAb2 alone (p=0.0005). In a next experiment, the effect of anti-IL-6R mAb1, an inhibitory anti-ErbB3 antibody ("anti-ErbB3 mAb3"), or a combination of anti-IL-6R mAb1 plus anti-ErbB3 mAb3 on the growth of A549 human lung adenocarcinoma xenografts was tested. Briefly, $1 \times 10^7$ A549 cells (ATCC, Cat. No. CCL-185) were implanted subcutaneously into the flank of 6-8 week old SCID mice (Taconic, Hudson, N.Y.). After tumors reached an average volume of 400 mm$^3$, mice were randomized into groups for treatment (n=6 mice per group). Mice were administered human Fc control protein (25 mg/kg), anti-IL-6R mAb1 (12.5 mg/kg), anti-ErbB3 mAb3 (12.5 mg/kg) or the combination of anti-IL-6R mAb1 plus anti-ErbB3 mAb3 (12.5+12.5 mg/kg). All proteins were administered via subcutaneous injection twice per week. Tumor volumes were measured twice per week over the course of the experiment (on days 59, 62, 66, 69, 74, 77, 80, 83, 87 and 90 after implantation) and tumor weights were determined upon excision of tumors at the conclusion of the experiment. Averages of the tumor growth from the start of treatment and the tumor weights were calculated for each group. The percent decreases of tumor growth and tumor weight were calculated from comparison to the Fc control group. The results are summarized in Tables 4 and 5.

TABLE 4

Inhibition of A549 tumor xenograft growth in SCID mice

| Antibody (mg/kg) | Tumor growth in mm$^3$ from start of treatment (mean ± SD) | Average % Decrease in Tumor Growth |
|---|---|---|
| hFc control (25) | 460.4 ± 234.0 | — |
| anti-IL-6R mAb1 (12.5) | 232.1 ± 191.8 | 50 |
| anti-ErbB3 mAb3 (12.5) | 108.5 ± 153.6 | 76 |
| anti-IL-6R mAb1 + anti-ErbB3 mAb3 (12.5 + 12.5) | −13.9 ± 188.2 | 103 |

TABLE 5

Change in A549 tumor xenograft weight in SCID mice

| Antibody (mg/kg) | Average Tumor Weight (g) | Average % Decrease in Tumor Weight |
|---|---|---|
| hFc control (25) | 1.30 ± 0.39 | — |
| anti-IL-6R mAb1 (12.5) | 0.96 ± 0.30 | 26 |
| anti-ErbB3 mAb3 (12.5) | 0.98 ± 0.32 | 25 |
| anti-IL-6R mAb1 + anti-ErbB3 mAb3 (12.5 + 12.5) | 0.72 ± 0.35 | 44 |

Finally, the effect of anti-IL-6R mAb1 on the growth of A549 human lung adenocarcinoma xenografts was investigated. Briefly, $5 \times 10^6$ A549 cells (ATCC, Cat. No. CCL-185) were implanted subcutaneously into the flank of 6-8 week old SCID mice (Taconic, Hudson, N.Y.). After tumors reached an average volume of ~100 mm$^3$, mice were randomized into groups for treatment (n=5 mice per group). Mice were administered human Fc control protein (25 mg/kg), anti-IL-6R mAb1 (2.5 mg/kg), or anti-IL-6R mAb1 (25 mg/kg). All proteins were administered via subcutaneous injection twice per week. Tumor volumes were measured twice per week over the course of the experiment. The average tumor growth from the start of treatment was calculated for each group. The percent decrease of tumor growth was calculated from comparison to the Fc control group. The results are summarized in Table 6.

TABLE 6

Inhibition of A549 tumor xenograft growth in SCID mice

| Antibody (mg/kg) | Tumor growth in mm$^3$ from start of treatment (mean ± SD) | Average % Decrease in Tumor Growth |
|---|---|---|
| hFc control (25) | 390.2 ± 51.3 | — |
| anti-IL-6R mAb1 (2.5) | 216.1 ± 106.2 | 45 |
| anti-IL-6R mAb1 (25) | 222.7 ± 21.9 | 43 |

Conclusion

This Example illustrates that anti-IL-6R mAb1 inhibited the growth of Du145, Calu3 and A549 tumor xenografts as a single agent. Furthermore, combination treatment with anti-IL-6R mAb1 plus VEGF-Trap inhibited the growth of Du145 tumor xenografts more potently than either single agent. Also, combination treatment with anti-IL-6R mAb1 plus an inhibitory anti-EGFR antibody (anti-EGFR mAb2) inhibited the growth of Calu3 tumor xenografts more potently than either single agent.

These results show that anti-IL-6R mAb1 preferentially inhibited the growth of tumors that exhibit autocrine IL-6/STAT3 signaling, suggesting the possibility that immunohistochemical analysis of tumor biopsies for IL-6 and/or phospho-STAT3 levels might be useful in identifying patients that are most likely to benefit from anti-IL-6R treatment. Moreover, anti-IL-6R mAb1 decreased phospho-STAT3 and increased cleaved caspase-3 levels in tumor xenografts, suggesting that IL-6/STAT3 signaling contributes to tumor cell survival.

Example 2

An Anti-IL-6R Monoclonal Antibody in Combination with a VEGF Antagonist Inhibits the Growth of Anti-VEGF-Resistant Tumors Introduction A variant of the A431 human epidermoid carcinoma cell line that is resistant to the effects of VEGF Trap was isolated by serial passage in the presence of VEGF-Trap in vivo. The variant cell line is referred to herein as "A431-V2," and the parental A431 cell line is referred to herein as "A431-P".

Figure 2:
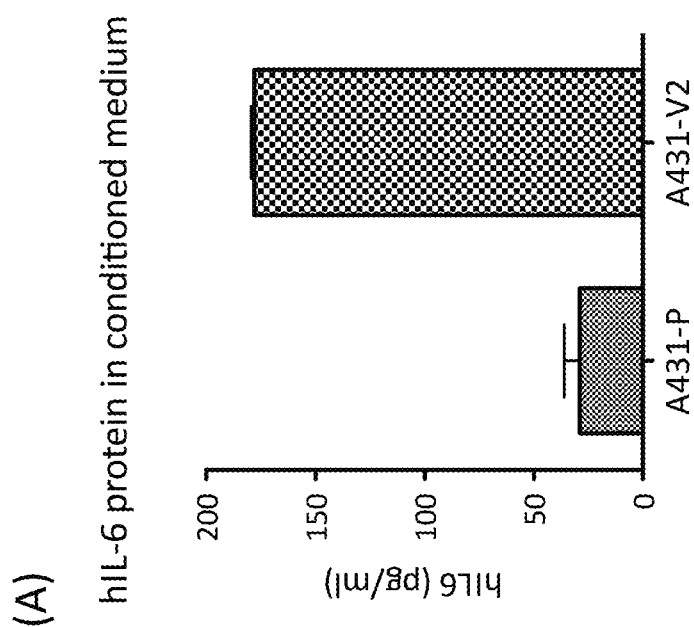
FIG. 2, panel A shows the results of an ELISA performed on conditioned medium collected from cultured A431-P or A431-V2 cells to measure the concentration of IL-6.

Experiments were first conducted to assess the relative levels of IL-6 expressed from the A431-V2 cell line as compared to the A431-P cell line. For this purpose, conditioned medium was collected from cultured A431-P or A431-V2 cells and ELISA was performed to measure the concentration of human IL-6. As shown in FIG. 2(a), A431-V2, expresses much higher levels of IL-6 than does the parental A431 cell line (178 µg/ml vs 29 µg/ml).

Next, the levels of phospho-STAT3 were measured in the variant and parental A431 cells. Specifically, cultured A431-P and A431-V2 cells were treated with human Fc (10 µg/ml) or anti-IL-6R mAb1 (10 µg/ml). Cell lysates were prepared and a Western blot was performed to assess the levels of phospho-STAT3. As shown in FIG. 2(b), the basal level of phospho-STAT3 was increased in A431-V2 cells as compared to A431-P cells, and was significantly reduced by anti-IL-6R mAb1 treatment.

In view of the foregoing experimental observations, the effect of a combination treatment comprising a fully human anti-IL-6R antibody plus VEGF-Trap on the growth of A431-V2 tumor xenografts was next tested in this Example.

Experimental Procedures and Results

Briefly, 1×10$^6$ A431-V2 cells were implanted subcutaneously into the flank of 6-8 week old SCID mice (Taconic, Hudson, N.Y.). After tumors reached an average volume of ~200 mm$^3$, mice were randomized into groups for treatment (n=5 mice per group). Mice were administered human Fc control protein (25 mg/kg), anti-IL-6R mAb1 (25 mg/kg), VEGF-Trap (25 mg/kg) or the combination of anti-IL-6R mAb1 plus VEGF-Trap (25+25 mg/kg). All proteins were administered via subcutaneous injection twice per week. Tumor volumes were measured twice per week over the course of the experiment (on days 15, 18, 22, 25 and 28 after implantation). The average tumor growth from the start of treatment was calculated for each group. The percent decrease of tumor growth was calculated from comparison to the Fc control group. The results are summarized in Table 7.

TABLE 7

Inhibition of A431-V2 tumor xenograft growth in SCID mice

| Antibody (mg/kg) | Tumor growth in mm$^3$ from start of treatment (mean ± SD) | Average % Decrease in Tumor Growth |
|---|---|---|
| hFc control (25) | 960.2 ± 201.0 | — |
| anti-IL-6R mAb1 (25) | 1006.1 ± 467.2 | −5 |
| VEGF-trap (25) | 615.8 ± 223.0 | 36 |
| anti-IL-6R mAb1 + VEGF-trap (25 + 25) | 240.8 ± 91.8 | 75 |

An analysis of the raw data underlying the results summarized in Table 7 confirmed that the tumor growth reduction observed in mice treated with the combination of anti-IL-6R mAb1+VEGF-trap was statistically significant in comparison to the change in tumor growth observed in mice treated with either anti-IL-6R mAb1 alone (p=0.0001) or VEGF-trap alone (p=0.0041).

Conclusion

As shown in this Example, A431-V2 tumors are resistant to VEGF-Trap single agent treatment, producing only a 36% decrease in tumor growth relative to control-treated subjects. These tumors, however, were responsive to anti-IL-6R mAb1 plus VEGF-Trap combination treatment, suggesting that IL-6 contributes to the VEGF-Trap-resistant phenotype of A431-V2 tumors. Preliminary data indicate that the increased IL-6 signaling in the A431-V2 tumors does not prevent the ability of VEGF-Trap to decrease tumor vascularity, suggesting that IL-6 signaling enhances the ability of tumor cells to proliferate and/or survive when the function of the tumor vasculature is impaired. This observation is consistent with the ability of anti-IL-6R mAb1 to potentiate the effect of VEGF-Trap in Du145 tumors as well (see Example 1).

In summary, the data presented herein above indicate that levels of IL-6/STAT3 signaling can be used to identify anti-VEGF-resistant tumors, and that IL-6 antagonism (e.g., treatment with anti-IL-6R mAb1) is a useful therapeutic strategy for treating multiple types of cancer, either as a single agent or in combination with VEGF antagonists, especially in the context of anti-VEGF-resistant tumors.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for inhibiting or attenuating the growth of an anti-VEGF-resistant tumor in a subject, the method comprising:
   (i) administering to the subject an anti-IL-6R antibody or antigen-binding fragment thereof; and
   (ii) administering to the subject a VEGF antagonist, wherein the subject has a tumor comprising an amount of phospho-STAT3 which is at least three times higher than a tumor sensitive to a VEGF antagonist by itself.

2. The method as claimed in claim 1, wherein the anti-IL-6R antibody or antigen-binding fragment thereof comprises a heavy chain variable region (HCVR) of SEQ ID NO: 2 and a light chain variable region (LCVR) of SEQ ID NO: 3.

3. The method of claim 1, wherein the VEGF antagonist is a fusion protein comprising Ig domain 2 of VEGFR1, Ig domain 3 of VEGFR2, and a multimerizing domain.

4. The method of claim 3, wherein the Ig domain 2 of VEGFR1 comprises amino acids 27 to 129 of SEQ ID NO:11, the Ig domain 3 of VEGFR2 comprises amino acids 130 to 231 of SEQ ID NO:11, and the multimerizing domain comprises amino acids 232 to 457 of SEQ ID NO:11.

5. The method as claimed in claim 1, wherein the tumor comprises an amount of phospho-STAT3 which is at least four times higher than in a tumor sensitive to a VEGF antagonist by itself.

6. The method as claimed in claim 1, wherein the tumor comprises an amount of phospho-STAT3 which is at least five times higher than in a tumor sensitive to a VEGF antagonist by itself.

7. The method as claimed in claim 1, wherein the tumor comprises an amount of phospho-STAT3 which is at least six times higher than in a tumor sensitive to a VEGF antagonist by itself.

8. The method as claimed in claim 1, wherein the tumor comprises an amount of phospho-STAT3 which is at least seven times higher than in a tumor sensitive to a VEGF antagonist by itself.

9. A method for inhibiting or attenuating the growth of an anti-VEGF-resistant tumor in a subject, the method comprising:
(i) administering to the subject an anti-IL-6R antibody or antigen-binding fragment thereof; and
(ii) administering to the subject a VEGF antagonist;
wherein the anti-IL-6R antibody or antigen-binding fragment thereof comprises a heavy chain variable region (HCVR) and a light chain variable region (LCVR), wherein the HCVR comprises CDRs having the amino acid sequences of SEQ ID NOs:4, 5, and 6; and wherein the LCVR comprises CDRs having the amino acid sequences of SEQ ID NOs:7, 8 and 9 wherein the subject has a tumor comprising an amount of phospho-STAT3 which is at least three times higher than in a tumor sensitive to a VEGF antagonist by itself.

10. The method as claimed in claim 9, wherein the tumor comprises an amount of phospho-STAT3 which is at least four times higher than in a tumor sensitive to a VEGF antagonist by itself.

11. The method as claimed in claim 9, wherein the tumor comprises an amount of phospho-STAT3 which is at least five times higher than in a tumor sensitive to a VEGF antagonist by itself.

12. The method as claimed in claim 9, wherein the tumor comprises an amount of phospho-STAT3 which is at least six times higher than in a tumor sensitive to a VEGF antagonist by itself.

13. The method as claimed in claim 9, wherein the tumor comprises an amount of phospho-STAT3 which is at least seven times higher than in a tumor sensitive to a VEGF antagonist by itself.

14. A method of inhibiting or attenuating the growth of an anti-VEGF-resistant tumor in a subject, the method comprising:
(i) administering to the subject an anti-IL-6R antibody or antigen-binding fragment thereof; and
(ii) administering to the subject a second therapeutic agent selected from the group consisting of:
(a) a fusion protein comprising Ig domain 2 of VEGFR1, Ig domain 3 of VEGFR2, and a multimerizing domain; and
an antibody selected from the group consisting of:
(b) an anti-EGFR antibody;
(c) an anti-EGFRvIII antibody;
(d) an anti-ErbB2 antibody;
(e) an anti-ErB3 antibody; and
(f) an anti-ErB4 antibody,
wherein the subject has a tumor comprising an amount of phospho-STAT3 which is at least three times higher than in a tumor sensitive to a VEGF antagonist by itself.

15. The method of claim 14, wherein the anti-IL-6R antibody or antigen-specific binding fragment thereof comprises a heavy chain variable region (HCVR) of SEQ ID NO: 2 and a light chain variable region (LCVR) of SEQ ID NO: 3.

16. The method of claim 14, wherein the second therapeutic agent is a fusion protein comprising Ig domain 2 of VEGFR1, Ig domain 3 of VEGFR2, and a multimerizing domain, wherein the Ig domain 2 of VEGFR1 comprises amino acids 27 to 129 of SEQ ID NO:11, the Ig domain 3 of VEGFR2 comprises amino acids 130 to 231 of SEQ ID NO:11, and the multimerizing domain comprises amino acids 232 to 457 of SEQ ID NO:11.

17. The method as claimed in claim 14, wherein the tumor comprises an amount of phospho-STAT3 which is at least four times higher than in a tumor sensitive to a VEGF antagonist by itself.

18. The method as claimed in claim 14, wherein the tumor comprises an amount of phospho-STAT3 which is at least five times higher than in a tumor sensitive to a VEGF antagonist by itself.

19. The method as claimed in claim 14, wherein the tumor comprises an amount of phospho-STAT3 which is at least six times higher than in a tumor sensitive to a VEGF antagonist by itself.

20. The method as claimed in claim 14, wherein the tumor comprises an amount of phospho-STAT3 which is at least seven times higher than in a tumor sensitive to a VEGF antagonist by itself.

21. A method of treating a subject with a tumor resistant to VEGF therapy, comprising:
administering to the subject a pharmaceutical formulation comprising:
a VEGF antagonist; and
an IL-6R antibody antagonist;
wherein the anti-IL-6R antibody antagonist comprises a heavy chain variable region (HCVR) of SEQ ID NO: 2 and a light chain variable region (LCVR) of SEQ ID NO: 3; and
wherein the VEGF antagonist is a fusion protein comprising Ig domain 2 of VEGFR1, Ig domain 3 of VEGFR2, and a multimerizing domain, wherein the Ig domain 2 of VEGFR1 comprises amino acids 27 to 129 of SEQ ID NO:11, the Ig domain 3 of VEGFR2 comprises amino acids 130 to 231 of SEQ ID NO:11, and the multimerizing domain comprises amino acids 232 to 457 of SEQ ID NO:11;
wherein the tumor comprises an amount of phospho-STAT3 which is at least four times higher than in a tumor sensitive to a VEFG antagonist by itself.

22. The method as claimed in claim 21, wherein the tumor comprises an amount of phospho-STAT3 which is at least five times higher than in a tumor sensitive to a VEGF antagonist by itself.

23. The method as claimed in claim 21, wherein the tumor comprises an amount of phospho-STAT3 which is at least six times higher than in a tumor sensitive to a VEGF antagonist by itself.

24. The method as claimed in claim 21, wherein the tumor comprises an amount of phospho-STAT3 which is at least seven times higher than in a tumor sensitive to a VEGF antagonist by itself.

* * * * *

SEQUENCE LISTING

<160> NUMBER OF SEQ ID NOS: 11

<210> SEQ ID NO 1
<211> LENGTH: 358
<212> TYPE: PRT
<213> ORGANISM: Homo sapiens

<400> SEQUENCE: 1

Met Val Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp
        355

```
<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Arg Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Arg Ile Gly Tyr Ala Asp Ser Val
    50                  55                  60

Lys Gly Arg Phe Thr Ile Ser Arg Asp Asn Ala Glu Asn Ser Leu Phe
65                  70                  75                  80

Leu Gln Met Asn Gly Leu Arg Ala Glu Asp Thr Ala Leu Tyr Tyr Cys
                85                  90                  95

Ala Lys Gly Arg Asp Ser Phe Asp Ile Trp Gly Gln Gly Thr Met Val
            100                 105                 110

Thr Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Arg Phe Thr Phe Asp Asp Tyr Ala
 1               5
```

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

Ile Ser Trp Asn Ser Gly Arg Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Ala Lys Gly Arg Asp Ser Phe Asp Ile
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic

<400> SEQUENCE: 7

Gln Gly Ile Ser Ser Trp
1               5

<210> SEQ ID NO 8
<211> LENGTH: 3
<212> TYPE: PRT
<213> ORGANISM: Artificial Sequence
<220> FEATURE:
<223> OTHER INFORMATION: Synthetic

<400> SEQUENCE: 8

Gly Ala Ser
1

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Gln Gln Ala Asn Ser Phe Pro Tyr Thr
1               5

<210> SEQ ID NO 10
<211> LENGTH: 1377
<212> TYPE: DNA
<213> ORGANISM: Homo sapiens

<400> SEQUENCE: 10
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240

-continued

```
cgcataatct gggacagtag aaagggcttc atcatatcaa atgcaacgta caaagaaata      300
gggcttctga cctgtgaagc aacagtcaat gggcatttgt ataagacaaa ctatctcaca      360
catcgacaaa ccaatacaat catagatgtg gttctgagtc cgtctcatgg aattgaacta      420
tctgttggag aaaagcttgt cttaaattgt acagcaagaa ctgaactaaa tgtggggatt      480
gacttcaact gggaataccc ttcttcgaag catcagcata agaaacttgt aaaccgagac      540 ctaaaaccc agtctgggag tgagatgaag aaattttga gcaccttaac tatagatggt       600
gtaacccgga gtgaccaagg attgtacacc tgtgcagcat ccagtgggct gatgaccaag     660
aagaacagca catttgtcag gtccatgaa aaggacaaaa ctcacacatg cccaccgtgc      720
ccagcacctg aactcctggg gggaccgtca gtcttcctct tccccccaaa acccaaggac     780
accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta acagcacg taccgtgtgg tcagcgtcct caccgtcctg       960
caccaggact ggctgaatgg caaggagtac aagtgcaagg tctccaacaa agccctccca    1020 gccccccatcg agaaaaccat ctccaaagcc aaagggcagc cccgagaacc acaggtgtac   1080
accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga       1377
```

<210> SEQ ID NO 11
<211> LENGTH: 458
<212> TYPE: PRT
<213> ORGANISM: Homo sapiens

<400> SEQUENCE: 11

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
             20                  25                  30

Phe Val Glu Met Tyr Ser Glu Ile Pro Glu Ile Ile His Met Thr Glu
         35                  40                  45

Gly Arg Glu Leu Val Ile Pro Cys Arg Val Thr Ser Pro Asn Ile Thr
     50                  55                  60

Val Thr Leu Lys Lys Phe Pro Leu Asp Thr Leu Ile Pro Asp Gly Lys
 65                  70                  75                  80

Arg Ile Ile Trp Asp Ser Arg Lys Gly Phe Ile Ile Ser Asn Ala Thr
                 85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

-continued

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
        210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```